US006933365B2

(12) United States Patent
Kumagai et al.

(10) Patent No.: US 6,933,365 B2
(45) Date of Patent: Aug. 23, 2005

(54) MUTANT TYROSINE REPRESSOR PROTEINS

(75) Inventors: Hidehiko Kumagai, Ohtsu (JP); Hideyuki Suzuki, Kyoto (JP); Takane Katayama, Kyoto (JP)

(73) Assignee: Ajinomoto Co., Inc., Tokyo (JP)

( * ) Notice: Subject to any disclaimer, the term of this patent is extended or adjusted under 35 U.S.C. 154(b) by 128 days.

(21) Appl. No.: 09/795,483

(22) Filed: Mar. 1, 2001

(65) Prior Publication Data

US 2002/0010136 A1 Jan. 24, 2002

(30) Foreign Application Priority Data

Mar. 1, 2000 (JP) ........................................ 2000-055886

(51) Int. Cl.[7] ................................................ C07K 1/00
(52) U.S. Cl. ...................................... 530/350; 530/825
(58) Field of Search ................................. 530/350, 825

(56) References Cited

U.S. PATENT DOCUMENTS 6,146,878 A    11/2000   Kumagai et al.

FOREIGN PATENT DOCUMENTS

JP          11-313672        11/1999

OTHER PUBLICATIONS

Cui et al. A mutational analysis of the structural basis for transcriptional activation and monomer–monomer interaction in the TyrR system of *Escherichia coli* K–12. J. Bacteriol. (1993) 175(6): 1777–1784.*
J.S. Hwang, et al., Journal of Bacteriology, vol. 179, No. 4, pps. 1051–1058, "Critical Base Pairs and Amino Acid Residues for Protein–DNA Interaction Between the TyrR Protein and *TyrP* Operator of *Escherichia coli*," Feb. 1997.
T. Katayama, et al., Appl. Environ. Microbiol., vol. 66, pps. 4764–4771, "Cloning and Random Mutagenesis of the *Erwinia herbicola* tyrR Gene for High–Level Expression of Tyrosine Phenol–Lyase," 2000.
T. Kwok, et al., Molecular Microbiology, vol. 17, No. 3, pps. 471–481, "Analysis of an *Escherichia coli* Mutant TyrR Protein With Impaired Capacity for Tyrosine–Mediated Repression, But Still Able to Activate at $_0{}^{70}$ Promoters," 1995.
A.J. Pittard, et al., Molecular Microbiology, vol. 5, No. 7, pps. 1585–1592, "TyrR Protein of *Escherichia coli* and Its Role as Repressor and Activator," 1991.
H. Suzuki, et al., Journal of Fermentation and Bioengineering, vol. 75, No. 2, pps. 145–148, "Cloning and Nucleotide Sequence of *Erwinia herbicola* AJ2982 Tyrosine Phenol–Lyase Gene," 1993.
J. Yang, et al., Journal of Bacteriology, vol. 178, No. 4, pps. 1120–1125, "Further Geneic Analysis of the Activation Function of the TyrR Regulatory Protein of *Escherichia coli*," Feb. 1996.
J. Yang, et al., Journal of Bacteriology, vol. 175, No. 6, pps. 1767–1776, "A Generic Analysis of Various Functions of the TyrR Protein of *Escherichia coli*," Mar. 1993.
J. Yang, et al., Journal of Bacteriology, vol. 175, No. 19, pps. 6372–6375, "Mutations in the tyrR Gene of *Escherichia coli* Which Affect TyrR–Mediated Activation But Not TyrR–Mediated Repression," Oct. 1993.

* cited by examiner

*Primary Examiner*—Kathleen Kerr
(74) *Attorney, Agent, or Firm*—Oblon, Spivak, McClelland, Maier & Neustadt, P.C.

(57) ABSTRACT

A gene coding for a mutant tyrosine repressor having increased positive regulatory activity for expression of the tyrosine phenol lyase gene compared with a tyrosine repressor not having mutation is obtained by introducing a mutation into a tyrosine repressor gene of *Erwinia herbicola*, introducing the gene into which the mutation is introduced into *Escherichia coli* expressing a lactose operon under the control of a promoter and enhancer of the tyrosine phenol lyase gene derived from *Erwinia herbicola*, and selecting a transformed strain having increased β-galactosidase activity.

18 Claims, 6 Drawing Sheets

US 6,933,365 B2

MUTANT TYROSINE REPRESSOR PROTEINS

TECHNICAL FIELD

The present invention relates to a mutant tyrosine repressor having an increased positive regulatory activity for expression of tyrosine phenol lyase gene, a gene coding for the same and utilization thereof. These are useful in the field of fermentation engineering, for example, production of tyrosine phenol lyase, L-3,5-dihydroxyphenylalanine (hereafter, also referred to as "L-DOPA") and so forth.

BACKGROUND ART

A tyrosine repressor is known to negatively regulate biosynthesis of aromatic amino acids such as tyrosine. Further, the structure of the tyrosine repressor gene of *Escherichia coli* has already been elucidated (E. C. Cornish et al., *J. Biol. Chem.*, 261, 403–410 (1986)).

L-DOPA is a precursor of dopamine, which is a nerve transmitter substance, and useful as a therapeutic agent for Parkinson's disease and so forth. L-DOPA has conventionally been manufactured by chemical synthesis. In recent years, however, L-DOPA is enzymatically synthesized from pyrocatechol and serine, or pyrocatechol, pyruvate and ammonia by using tyrosine phenol lyase.

Tyrosine phenol lyase is known to be produced by a wide variety of microorganisms belonging to the genus *Escherichia, Pseudomonas, Flavobacterium, Bacillus, Serratia, Xanthomonas, Agrobacterium, Achromobacter, Aerobacter, Erwinia, Proteus, Salmonella, Citrobacter, Enterobacter* or the like (Japanese Patent No. 2521945, Japanese Patent Publication (Kokoku) No. 6-98003). Its enzymatic characteristics have also been elucidated (*Biochem. Biophys. Res. Commun.*, 33, 10 (1963)).

There were reported a structural gene and nucleotide sequence of an upstream region of tyrosine phenol lyase gene of bacteria belonging to the genus *Erwinia* known to highly express tyrosine phenol lyase (H. Suzuki et al., *J. Ferment. Bioeng.*, 75, No.2, 145–148 (1993)). Moreover, the inventors of the present invention successfully isolated a gene coding for a tyrosine repressor from the aforementioned bacteria and disclosed that the tyrosine repressor had positive regulatory activity for expression of the tyrosine phenol lyase gene (Japanese Patent Laid-Open Publication (Kokai) No. 11-313672).

It was also reported that the mtr and tyrP+4 promoters were activated about two times by substitution of a glycine residue for aspartic acid residue at a position of 97 and substitution of a phenylalanine residue for the aspartic acid residue at a position of 117 in the *Escherichia coli* tyrR gene (*J. Bacteriol.*, 178, 1120–1125 (1996)).

DISCLOSURE OF THE INVENTION

An object of the present invention is to develop a novel technique utilizing a tyrosine repressor gene. Specifically, an object of the present invention is to provide a mutant tyrosine repressor having an increased positive regulatory activity for expression of tyrosine phenol lyase gene, a gene for coding the same and a method of utilizing these.

The inventors of the present invention introduced various mutations into the tyrosine repressor gene and analyzed activity of the obtained mutant tyrosine repressors. As a result, the inventors of the present invention successfully obtained a gene coding for a mutant tyrosine repressor having an increased positive regulatory activity for expression of tyrosine phenol lyase gene compared with a wild-type tyrosine repressor, and accomplished the present invention.

That is, the present invention provides a mutant tyrosine repressor at least having one or more mutations selected from replacement of valine residue at a position of 67 with an amino acid residue other than valine residue, replacement of tyrosine residue at a position of 72 with an amino acid residue other than tyrosine residue, replacement of aspartic acid residue at a position of 97 with an amino acid residue other than aspartic acid residue and replacement of isoleucine residue at a position of 402 with an amino acid residue other than isoleucine residue and having an increased positive regulatory activity for expression of tyrosine phenol lyase gene compared with a tyrosine repressor not having those mutations.

The present invention also provides DNA coding for the aforementioned mutant tyrosine repressor.

The present invention further provides a bacterium belonging to the genus *Escherichia* or *Erwinia* harboring a structural gene of tyrosine phenol lyase operatively ligated to a promoter of the tyrosine phenol lyase gene and having ability to produce a product of the structural gene, which further harbors DNA coding for the aforementioned mutant tyrosine repressor, and in which expression of the structural gene is positively regulated by the mutant tyrosine repressor produced by the DNA.

The present invention also provides a method for producing tyrosine phenol lyase, comprising the step of culturing the aforementioned bacterium belonging to the genus *Escherichia* or *Erwinia* in a medium to produce tyrosine phenol lyase.

The present invention further provides a method for producing L-3,4-dihydroxyphenylalanine, comprising the steps of producing tyrosine phenol lyase by culturing the aforementioned bacterium belonging to the genus *Escherichia* or *Erwinia* in a medium to produce tyrosine phenol lyase and allowing the produced tyrosine phenol lyase to act on pyrocatechol and serine or pyrocatechol, pyruvic acid and ammonia to produce L-3,4-dihydroxyphenylalanine.

In the present specification, a tyrosine repressor having the aforementioned mutations will be also referred to as a mutant tyrosine repressor, and the DNA coding for the mutant tyrosine repressor will be also referred to as a mutant tyrosine repressor gene. A tyrosine repressor not having the mutations will be also referred to as a wild-type tyrosine repressor.

The present invention provides a mutant tyrosine repressor having an increased positive regulatory activity for expression of tyrosine phenol lyase gene compared with a tyrosine repressor not having the aforementioned mutations and DNA coding for it.

The mutant tyrosine repressor gene of the present invention can be utilized for regulating expression of a gene coding for a protein such as tyrosine phenol lyase. Further, tyrosine phenol lyase produced according to the present invention can be utilized for production of L-DOPA.

The present invention will be explained in detail hereinafter.

The mutant tyrosine repressor of the present invention has at least one or more mutations selected from replacement of valine residue at a position of 67 with an amino acid residue other than valine residue, replacement of tyrosine residue at a position of 72 with an amino acid residue other than tyrosine residue, replacement of aspartic acid residue at a position of 97 with an amino acid residue other than aspartic acid residue and replacement of isoleucine residue at a position of 402 with an amino acid residue other than isoleucine residue and has an increased positive regulatory activity for expression of the tyrosine phenol lyase gene compared with a tyrosine repressor not having these mutations.

Alanine residue can be mentioned as the amino acid residue other than valine residue. Cysteine residue can be mentioned as the amino acid residue other than tyrosine residue. Glycine residue can be mentioned as the amino acid residue other than aspartic acid residue. Valine residue can be mentioned as the amino acid residue other than isoleucine residue.

As the mutant tyrosine repressor of the present invention, there can be mentioned, specifically, a mutant tyrosine repressor having any of (a) replacement of valine residue at a position of 67 with an alanine residue (V67A), (b) replacement of tyrosine residue at a position of 72 with a cysteine residue (Y72C), (c) replacement of valine residue at a position of 67 with an alanine residue and replacement of tyrosine residue at a position of 72 with a cysteine residue (V67A, Y72C), and (d) replacement of valine residue at a position of 67 with an alanine residue, replacement of tyrosine residue at a position of 72 with a cysteine residue and replacement of glutamic acid residue at a position of 201 with a glycine residue (V67A, Y72C, E201G).

Except for these mutations, the mutant tyrosine repressor of the present invention may have the same amino acid sequence as that of a tyrosine repressor, for example, a wild-type tyrosine repressor derived from *Erwinia herbicola*. As an amino acid sequence of wild-type tyrosine repressor, the amino acid sequence shown as SEQ ID NO: 2 can be mentioned. In addition to the aforementioned mutations, the mutant tyrosine repressor may have other mutations for increasing positive regulatory activity for expression of tyrosine phenol lyase gene.

The mutant tyrosine repressor of the present invention can be obtained by introducing, into DNA coding for a wild-type tyrosine repressor, mutations for increasing positive regulatory activity for expression of the tyrosine phenol lyase gene of tyrosine repressor encoded by the DNA. As a wild-type tyrosine repressor, the tyrosine repressor derived from *Erwinia herbicola* can be mentioned. As DNA coding for a wild-type tyrosine repressor derived from *Erwinia herbicola*, there can be mentioned DNA having the nucleotide sequence shown as SEQ ID NO: 1. The mutation can be systematically introduced by site-directed mutagenesis or the like.

The mutant tyrosine repressor of the present invention may be a mutant tyrosine repressor including replacement, deletion, insertion, addition or inversion of one or several amino acids at positions other than the aforementioned mutations and having an increased positive regulatory activity for expression of tyrosine phenol lyase gene compared with a tyrosine repressor not having these mutations. The number of meant by the term "several", used herein may differ depending on the position and type of amino acid residues in the three-dimensional structure of the protein. This is because there are highly analogous amino acids for some amino acids and a replacement among such amino acids does not substantially affect the three-dimensional structure of the protein. Therefore, the mutant tyrosine repressor may be one having homology of 30–50% or more, preferably 50–70% or more, more preferably 80% or more, with respect to the whole amino acid sequence of the 521 amino acid residues constituting a tyrosine repressor, and having positive regulatory activity for expression of tyrosine phenol lyase gene.

In the present invention, the numbers used for the valine residue at a position of 67, the tyrosine residue at a position of 72, the aspartic acid residue at a position of 97 and the isoleucine residue at a position of 402 represent positions in the amino acid sequence of wild-type tyrosine repressor shown as SEQ ID NO: 2. These positions may be shifted ahead or backward by deletion, insertion, addition or inversion of one or more amino acids that do not affect the aforementioned activity. For example, if one amino acid residue is inserted into the N-terminal sequence, the valine residue that originally located at the 67th position shifts to the 68th position. In the present invention, such a valine residue equivalent to the valine residue at a position of 67 is referred to as the 67th valine residue.

DNA coding for a protein substantially equivalent to the aforementioned mutant tyrosine repressor can be obtained by modifying a nucleotide sequence, for example, by means of site-directed mutagenesis so that the amino acid sequence should contain substitution, deletion, insertion, addition or inversion of one or more amino acid residues at a specific site. The aforementioned modified DNA can also be obtained by a conventionally known mutagenesis treatment. As the mutagenesis treatment, there can be mentioned a method of treating DNA coding for tyrosine repressor in vitro with hydroxylamine or the like, a method of irradiating microorganisms harboring DNA coding for a tyrosine repressor, for example, bacteria belonging to the genus *Erwinia* with ultraviolet ray or treating these bacteria with a mutagenesis agent usually used for mutation treatment such as N-methyl-N'-nitro-N-nitrosoguanidine (NTG) and nitrous acid, and so forth.

The aforementioned substitution, deletion, insertion, addition, inversion or the like of nucleotides includes those mutations naturally occurring based on the difference in genera, species or individual difference in strains of the microorganism harboring a tyrosine repressor (mutant or variant).

DNA coding for a protein substantially equivalent to the mutant tyrosine repressor can be obtained by expressing DNA having the aforementioned mutations in an appropriate cell and investigating tyrosine repressor activity (positive regulatory activity for expression of the tyrosine phenol lyase gene) of the expressed product. DNA coding for a protein substantially equivalent to the mutant tyrosine repressor can also be obtained by isolating DNA which hybridizes with, for example, DNA having a nucleotide sequence of nucleotide numbers 442–2004 in the nucleotide sequence shown as SEQ ID NO: 1 in Sequence Listing under a stringent condition, and codes for a protein having a tyrosine repressor activity, from DNA coding for a tyrosine repressor having mutations or a cell harboring such DNA. The term "stringent condition" used herein refers to a condition under which a so-called specific hybrid is formed but a nonspecific hybrid is not formed. Although clear numeric conversion of this condition is difficult, for example, there can be mentioned a condition under which two of DNA's having high homology, for example, homology not less than 50%, are hybridized with each other, whereas DNA's having homology lower than that level are not hybridized or a condition under which DNA's hybridize under a normal washing condition of Southern hybridization, i.e., salt concentrations equivalent to 1×SSC, 0.1% SDS, preferably 0.1×SSC, 0.1% SDS, at 65° C.

Genes hybridized under these conditions include those in which a stop codon has been generated in the genes and those of which activity has been reduced or lost due to mutations at the active center, but these can be readily eliminated by ligating them to a commercially available expression vector and measuring the tyrosine repressor activity of expression products.

The tyrosine repressor gene derived from *Erwinia herbicola* can be selected from a chromosomal gene library of *Erwinia herbicola* by using *Escherichia coli* in which its own tyrosine repressor gene is deleted and which expresses the lactose operon under the control of a promoter and an enhancer of the tyrosine phenol lyase gene derived form *Erwinia herbicola* as a host according to the method described in Japanese Patent Laid-Open Publication (Kokai) No. 11-313672.

Further, since the structure of the tyrosine repressor gene of *Erwinia herbicola* was already elucidated (SEQ ID NO: 1), a tyrosine repressor gene can be obtained from chromosomal DNA or a chromosomal gene library of *Erwinia herbicola* by PCR or hybridization utilizing oligonucleotides prepared based on the sequence.

Microorganisms that have hitherto been classified into *Erwinia herbicola* are reclassified in *Pantoea agglomerans* at present. The genus *Erwinia* is very closely relative to the genus *Pantoea*, and therefore the tyrosine repressor gene can be obtained from microorganisms belonging to either the genus *Erwinia* or *Pantoea*.

The tyrosine repressor gene can be obtained as described above from bacteria belonging to a genus other than the genus *Erwinia* or *Pantoea*, for example, *Escherichia* bacteria such as *Escherichia coli*. The tyrosine repressor of *Escherichia coli* shows homology of about 72% with respect to the tyrosine repressor of *Erwinia herbicola*. In particular, the 67th valine residue is commonly conserved in both of the tyrosine repressors of *Escherichia coli* and *Erwinia herbicola*. Therefore, it is highly possible that the positive regulatory activity for expression of the tyrosine phenol lyase gene is increased by introducing a mutation at the 67th position of the tyrosine repressor of *Escherichia coli*. The present invention can be applied to a tyrosine repressor having such a degree of homology, preferably not less than 70%, more preferably not less than 80%, with the tyrosine repressor of *Erwinia herbicola*.

The mutant tyrosine repressor gene described in the examples mentioned hereinafter was obtained by randomly introducing mutations into the tyrosine repressor gene of *Erwinia herbicola* obtained as described above by error-prone PCR, introducing the resultant gene introduced with the mutations into *Escherichia coli* expressing a lactose operon under the control of the promoter and enhancer of the tyrosine phenol lyase gene derived from *Erwinia herbicola*, culturing the bacterium in a medium which contains X-gal (5-bromo-4-chloro-3-indolyl-β-D-galactoside) but does not contain tyrosine, and selecting a colony exhibiting a darker blue color compared with other colonies.

The mutant tyrosine repressor of the present invention and the gene coding for it can be utilized for regulating expression of a target gene. For example, expression of a target protein is positively regulated by the mutant tyrosine repressor by operatively ligating a structural gene coding for the protein to a promoter of the tyrosine phenol lyase gene, introducing the obtained fusion gene into a microorganism, and further introducing the mutant tyrosine repressor gene of the present invention into the microorganism.

Therefore, a target protein can be efficiently produced by culturing in a medium a microorganism introduced with a fusion gene of a promoter of tyrosine phenol lyase gene and a structural gene of the target protein and a mutant tyrosine repressor gene. If DNA coding for tyrosine phenol lyase is used as the structural gene of the target protein, tyrosine phenol lyase can be produced. Tyrosine phenol lyase can be utilized for enzymatic production of L-DOPA. That is, L-DOPA can be produced by steps of culturing the aforementioned microorganism in a medium to produce tyrosine phenol lyase and allowing the produced tyrosine phenol lyase to act on pyrocatechol and serine or pyrocatechol, pyruvate and ammonia to produce L-3,4-dihydroxyphenylalanine.

As the microorganism, there can be used bacteria belonging to the genus *Escherichia* or *Erwinia*. As an example of *Escherichia* bacteria, *Escherichia coli* can be mentioned. As an example of bacteria belonging to the genus *Erwinia*, *Erwinia herbicola* can be mentioned.

Tyrosine is normally required as an inducer of expression of the tyrosine phenol lyase gene in bacteria belonging to the genera *Escherichia* and *Erwinia*. However, expression of the tyrosine phenol lyase gene is induced in bacteria belonging to the genus *Escherichia* or *Erwinia* harboring the mutant tyrosine repressor gene of the present invention even when no or a little amount of tyrosine is added to a medium. Therefore, the amount of tyrosine used can be reduced.

To introduce the fusion gene or the mutant tyrosine repressor gene into microorganisms such as bacteria belonging to the genus *Escherichia* or *Erwinia*, recombinant DNA is usually prepared by ligating the genes to an appropriate vector. As the vector, there can be mentioned pUC19, pUC18, pBR322, pHSG299, pHSG399, pHSG398, RSF1010, pACYC177, pACYC184, pMW219, pMW118 and so forth.

Transformation methods reported so far can be employed to introduce the recombinant DNA prepared as described above into bacteria belonging to the genus *Escherichia* or *Erwinia*. For example, a method of increasing permeability of DNA by treating a recipient bacterium cell with calcium chloride has been reported for *Escherichia coli* K-12 (Mandel, M. and Higa, A., *J. Mol. Biol.*, 53, 159 (1970)), and a method of introducing DNA by preparing a competent cell from a cell at the growth stage has been reported for *Bacillus subtilis* (Duncan, C. H., Wilson, G. A. and Young, F. E., *Gene*, 1, 153 (1977)). Or, also employable is a method of introducing recombinant DNA into a DNA recipient bacterium by making a cell of the DNA recipient bacterium into a protoplast or spheroplast, which can easily take up recombinant DNA. This method is known to be applicable to *Bacillus subtilis*, actinomycetes and yeast (Chang, S. and Choen, S. N., *Molec. Gen. Genet.*, 168, 111 (1979); Bibb, M. J., Ward, J. M. and Hopwood, O. A., *Nature*, 274, 398 (1978); Hinnen, A., Hicks, J. B. and Fink, G. R., *Proc. Natl. Acad. Sci. USA*, 75, 1929 (1978)). Electroporation (Methods for general and molecular bacteriology, 1994, Philipp Gerhardt ed., ASM Press, 14.1.3.3 Electroporation procedure) can also be used.

Introduction of the fusion gene and the mutant tyrosine repressor gene may be carried out separately by using different vectors or both of the genes may be carried on the same vector by using a single vector. The order of introductions of the genes is not particularly limited.

The fusion gene and/or the mutant tyrosine repressor gene may be present on a plasmid of host microorganism or may be introduced into chromosomal DNA of host microorganism by homologous recombination or the like.

Expression of the introduced mutant tyrosine repressor gene may be controlled by a promoter proper to the tyrosine repressor gene. Or, the promoter may be replaced with a stronger promoter such as lac promoter, trp promoter, trc promoter, tac promoter, $P_R$ promoter or $P_L$ promoter of lamda phage, tet promoter and amyE promoter to control the expression by these promoters.

Ordinary methods known to those skilled in the art can be employed for preparation of chromosomal DNA, preparation of chromosomal DNA library, hybridization, PCR, preparation of plasmid DNA, cleavage and ligation of DNA, transformation, design of oligonucleotides used as primers and so forth. These methods are described in Sambrook, J., Fritsch, E. F., and Maniatis, T., "Molecular Cloning A Laboratory Manual, Second Edition", Cold Spring Harbor Laboratory Press, (1989) and so forth.

BEST MODE FOR CARRYING OUT THE INVENTION

Hereafter, the present invention will be explained more specifically with reference to the following examples.

EXAMPLE 1
Aguisition of Tyrosine Repressor Gene of *Erwinia herbicola*
<1> Preparation of Chromosomal Gene Library Derived from *Erwinia herbicola*

In an amount of 1.45 mg of chromosomal DNA was extracted from the *Erwinia herbicola* AJ2985 strain (ATCC21434) according to the method described in "Current protocols in molecular biology 2.4.1" (A. M. Frederick et al., Massachusetts General Hospital, Harvard Medical School, John Wiley & Sons, Inc., 1994). 43.5 μg of the obtained DNA was partially digested with 6 units of Sau3AI for 10 minutes or 15 minutes in 50 μl of a reaction system and subjected to agarose gel electrophoresis to recover 5.1 μg of DNA fragments of about 4–8 kbs.

Further, 5 μg of pBR322 (Toyobo) was digested with 10 units of BamHI for 2 hours and it was confirmed by agarose gel electrophoresis analysis that DNA was completely digested. Then, the 5' end was dephosphorylated with 2 units of alkaline phosphatase (Toyobo) at 37° C. for 1 hour to obtain about 3 μg of BamHI-digested DNA of pBR322.

1.4 μg of the pBR322 DNA prepared as described above and 1.7 μg of the DNA fragments of about 4–8 kbs were ligated in 80 μl of a reaction system by using a DNA ligation kit (TAKARA ligation kit Ver.2, Takara Shuzo) at 16° C. for 1 hour to obtain a chromosomal gene library derived from *Erwinia herbicola*.

<2> Preparation of Host for Screening (*E. coli* TK453)

As a host for screening plasmid clones containing the tyrosine repressor gene (tyrR), prepared was *Escherichia coli* which lacked its inherent tyrosine repressor gene and further carried on its chromosome a gene expressing a lactose operon under control of a promoter and enhancer of the tyrosine phenol lyase gene (tpl) derived from *Erwinia herbicola*.

The lactose operon was prepared from pRS552 (R. W. Simons et al., Gene, 53, 85–96 (1987)). The pRS552 is a plasmid harboring an incomplete lac operon lacking a part of the N-terminal of lacZ in the lactose operon. By ligating a gene fragment containing the N-terminal and the upstream region of the tyrosine phenol lyase gene (tpl) to this plasmid to match the reading frames, there was formed a fusion gene expressing a fusion protein (tpl'-'lac fusion protein) of the N-terminal portion (tpl') of tyrosine phenol lyase and C-terminal portion ('lacZ) of β-galactosidase lacking a part of the N-terminal under the control of tpl. This makes it possible to examine transcription regulation of tpl in *Escherichia coli* by using the β-galactosidase activity as a marker.

The promoter/enhancer region of tpl was prepared from the plasmid pSH768 containing that region (H. Suzuki et al., J. Ferment. Biol., 75, 145–148 (1993)).

Figure 1:
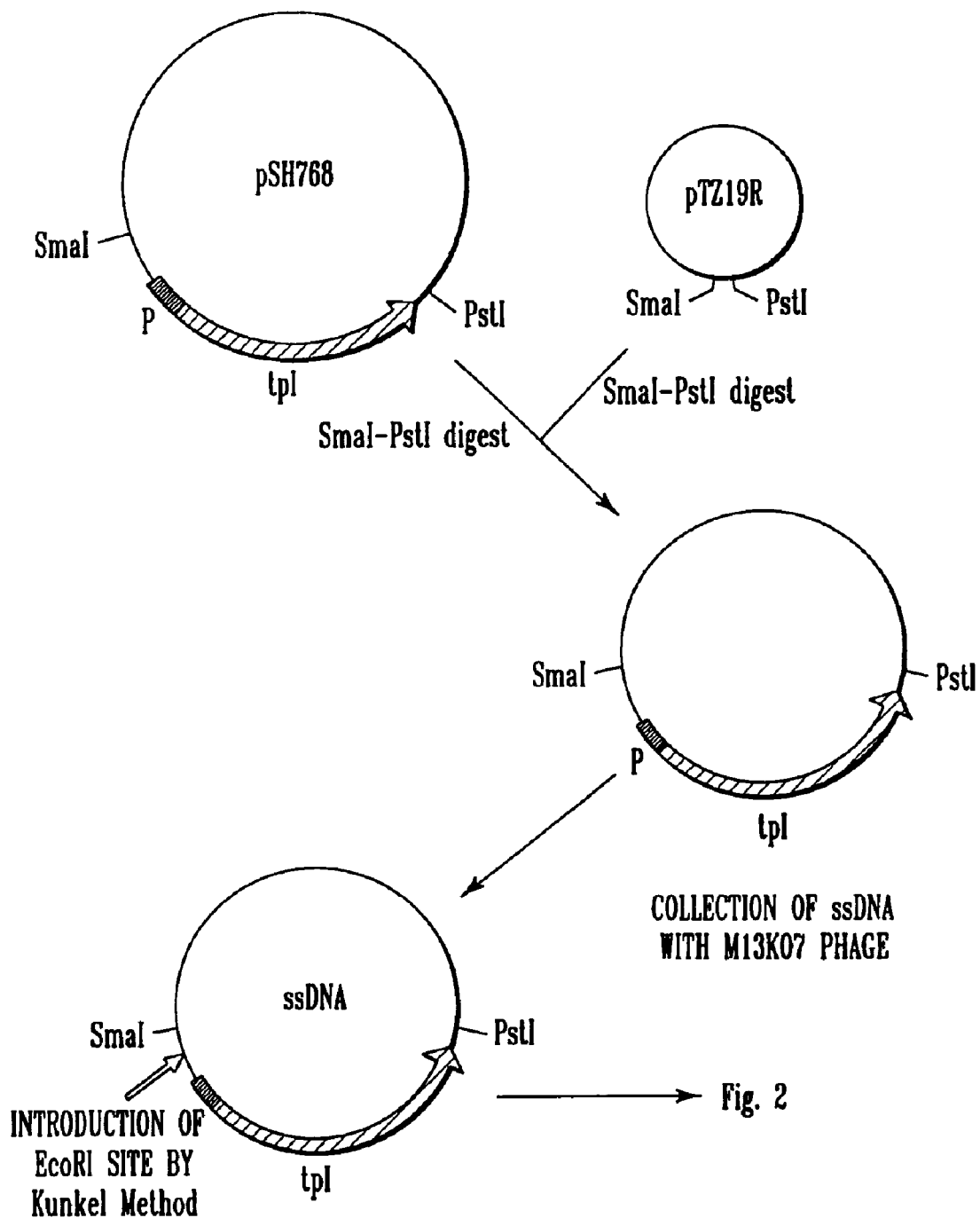
FIG. 1 shows a part of construction process of a plasmid introduced with a gene coding for the tpl'-'lac fusion protein (pTK312).
Figure 2:
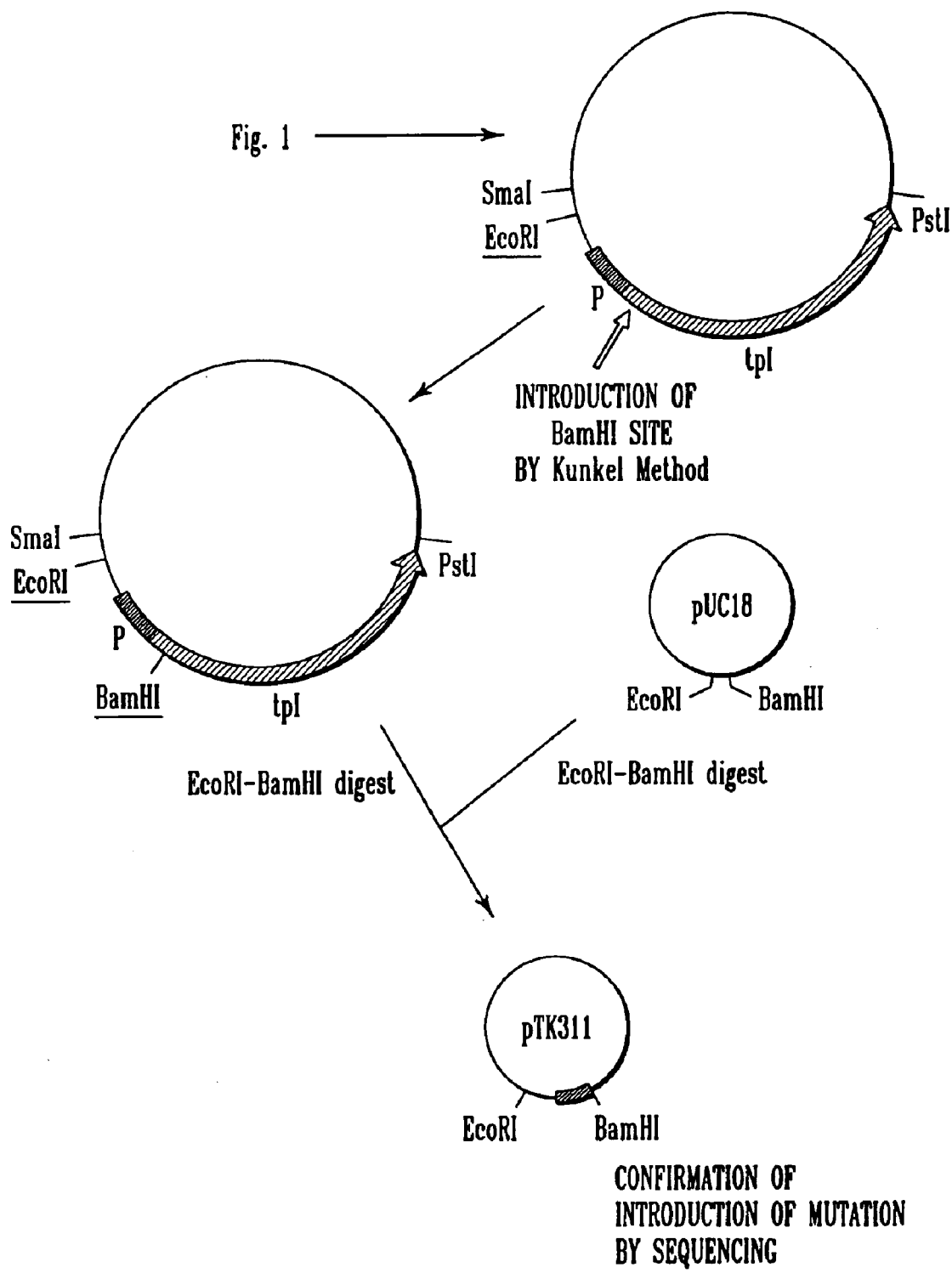
FIG. 2 shows a part of construction process of a plasmid introduced with a gene coding for the tpl'-'lac fusion protein (pTK312).
Figure 3:
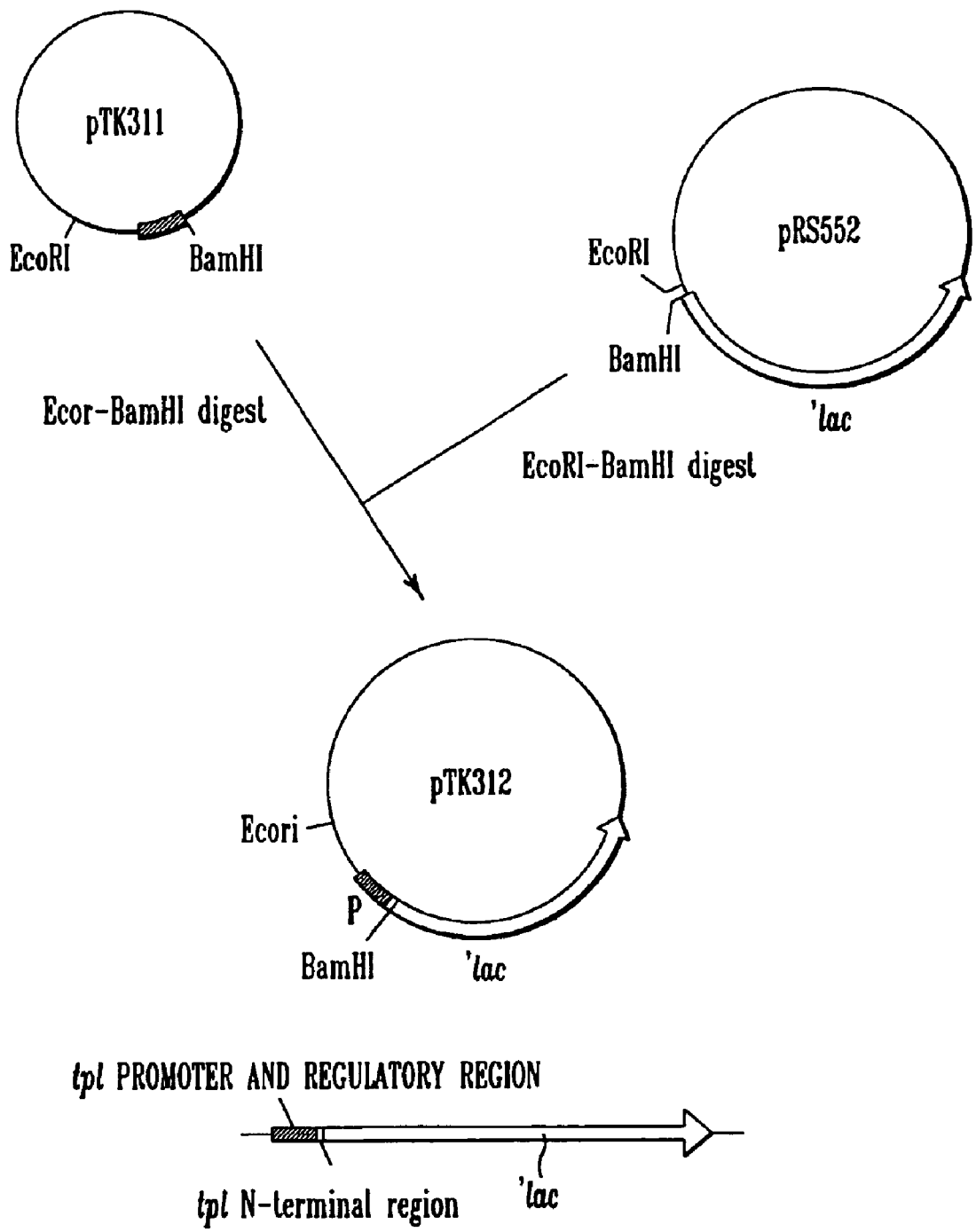
FIG. 3 shows a part of construction process of a plasmid introduced with a gene coding for the tpl'-'lac fusion protein (pTK312).

First, a plasmid for introducing the fusion gene into *Escherichia coli* was constructed (FIGS. 1–3). The sequence atgaactatcc (SEQ ID NO: 3) corresponding to the N-terminal of tpl in pSH768 was modified to atgaaggatcc (SEQ ID NO: 4, introduction of BamHI site) by site-directed mutagenesis. The sequence ttaacattcgc (SEQ ID NO: 5) located about 480 bps upstream from the N-terminal was modified to ttagaattcgc (SEQ ID NO: 6, introduction of EcoRI site). Specifically, these mutageneses were carried out as follows. pSH768 was digested with SmaI and PstI to prepare a 2.2-kb SmaI-PstI fragment. This fragment was inserted between the SmaI and PstI sites of pTZ19R (Pharmacia) (FIG. 1). A site-directed mutation was introduced by the method of Kunkel (Kunkel, T. A., Proc. Natl. Acad. Sci. USA, 82, 488–492 (1985), Kunkel, T. A., Methods in Enzymology, 154, 367–382 (1987)) by using a site-directed mutagenesis kit (Muta-gene phagemid in vitro mutagenesis kit instruction manual (Bio-Rad)) (FIG. 1 and upper portion of FIG. 2). The oligonucleotide sequences used for introductions of the BamHI site and EcoRI site were 5'-tcggcaggatccttcatgttta-3' (SEQ ID NO: 7) and 5'-agcggcgaattctaatgacgtg-3' (SEQ ID NO: 8), respectively.

Subsequently, an about 480-bps gene fragment excised with EcoRI and BamHI was inserted between the EcoRI and BamHI sites of pUC18 (pTK311), and then the nucleotide sequence of the inserted fragment portion was determined to confirm that EcoRI and BamHI sites were correctly created at the target sites (FIG. 2). After the confirmation, the gene fragment of about 480 bps excised with EcoRI and BamHI was inserted between the EcoRI and BamHI sites of pRS552 to prepare a plasmid (pTK312) containing a gene coding for the tpl'-'lac fusion protein (FIG. 3).

Then, the *E. coli* TE2680 strain (T. Elliott, J. Bacteriol., 174, 245–253 (1992)) was transformed with the plasmid pTK312 containing the tpl'-'lac fusion gene. The transformation and preparation of a competent cell used for the transformation were carried out according to Hiroaki Inoue and Hiroshi Nojima, "Preparation Method of Gene Library", p19–26, 1995 (Yodosha). Since homologous regions (kanamycin resistant gene and lac gene) are present on the chromosomes of pTK312 (derived from pRS552) and TE2680, homologous recombination occurs at a certain frequency. As a result, a strain containing a gene coding for the tpl'-'lac fusion protein as a single copy on the chromosome can be prepared. The strain thus obtained was designated as TK314.

The aforementioned TK314 carries recD (since the exonuclease activity of exonuclease V is deleted, linear DNA is not digested in the cell), and hence a plasmid is not stably replicated in such a strain. Therefore, it is difficult to use this as a host of a chromosomal gene library derived from *Erwinia herbicola*. Accordingly, neighboring genes containing the gene coding for the tpl'-'lac fusion protein in TK314 were transduced into *E. coli* JM107 by P1 transduction (A Short Course in Bacterial Genetics, J. H. Miller, Cold Spring Harbor Laboratory Press, Cold Spring Harbor N.Y. 1992).

Since it was suggested that a gene coding for the tpl'-'lac fusion protein was activated by a tyrosine repressor (TyrR) of *E. coli* (H. Suzuki et al., *Biosci. Biotech. Biochem.*, 59, 2339–2341 (1995), H. Q. Smith et al., *J. Bacteriol.*, 179, 5914–5921 (1997)), tyrR366 (H. Camakaris et al., *J. Bacteriol.*, 115, 1135–1144 (1973)) was introduced by P1 transduction to inactivate functions of the chromosome tyrR of *E. coli* JM107. Finally, Δ(srl-recA)306::Tn10 was introduced from MV1184 (*Methods in Enzymology*, 153, 3–11 (1987)) to make the cell recA⁻ and it was designated as TK453. A competent cell was prepared with this TK453, and used as a host for screening of a chromosomal gene library derived from *Erwinia herbicola*.

<3> Screening of Chromosomal Gene Library for Gene Activating Expression of tpl'-'lac Fusion Protein Gene TK453 was transformed by using 8 μl of the library prepared as described above and then plated on a MacConkey-Lactose medium (Difco) containing 5 mM L-tyrosine to obtain about 20,000 colonies. Among these, 23 colonies exhibited a phenotype of red color, which is a marker of expression of β-galactosidase gene (lacZ). It was considered from this phenotype that the target tyrR or β-galactosidase gene was contained in the chromosomal DNA fragment inserted into the plasmid introduced into these colony cells, but there was also a possibility that other unknown genes were contained.

Figure 4:
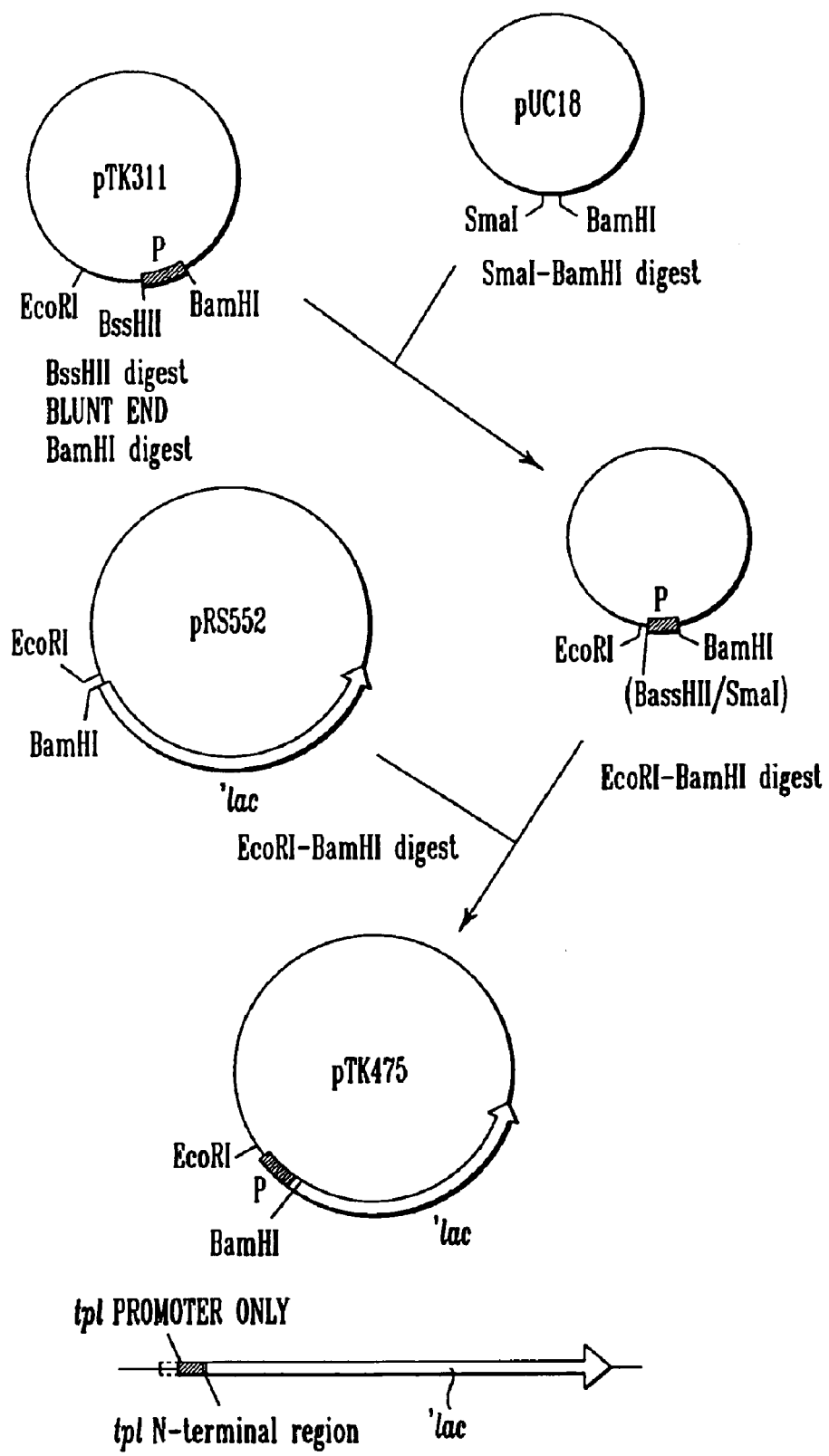
FIG. 4 shows construction of a plasmid (pTK475) containing the tpl'-'lac fusion protein gene from which a regulatory region is removed.

Therefore, for further confirmation, a strain (TK481) having the tpl'-'lac fusion protein gene lacking a regulatory region located upstream from the promoter of tpl, which is considered to be bound to a regulatory protein such as TyrR, was prepared. That is, the plasmid pTK311 was treated with BssHII and blunt-ended. Further, the plasmid was digested with BamHI to excise a 180-bps BssHII-BamHI fragment. This fragment was inserted between the SmaI and BamHI sites of pUC18 and the obtained plasmid was digested with EcoRI and BamHI to prepare an about 190-bps fragment. This fragment was ligated with pRS552 digested with EcoRI and BamHI (pTK475) (FIG. 4). Subsequently, *E. Coli* TE2680 was transformed with the obtained pTK475, and chromosomal homologous recombination was performed in the same manner as described above to obtain TK481.

Since the upstream regulatory region was removed in TK481, proteins involved in the control of tpl expression could not function. It is considered that, as a result, the tpl'-'lac fusion protein gene was scarcely expressed. Therefore, a plasmid was prepared from a strain exhibiting a phenotype of red color in a primary screening, and TK481 was transformed with the plasmid. Then, those exhibiting a phenotype of white color were selected. Twenty strains were obtained by this secondary screening. An about 1.6-kb DNA fragment was detected for all of the plasmids of these strains when they were treated with EcoRI. All of these transformants exhibited sensitivity to 3-fluorotyrosine (tyrR⁻ makes *E. coli* resistant to 3-fluorotyrosine, H. Camakaris et al., *J. Bacteriol.*, 115, 1135–1144 (1973)), and showed the same property as the phenotype of tyrR⁺ in *E. coli*. From these results, it was strongly suggested that these clones had a DNA fragment containing the same certain DNA region, and they contained tyrR derived from *Erwinia herbicola*.

From the above candidate strains, one plasmid having tyrR was designated as pTK-#20 and used in the following experiment. An about 2 kb or longer gene fragment obtained by treatment with various restriction enzymes (EcoRI, BssHIII, EcoRV, HpaI, SalI, SphI, NruI and so forth) to further shorten the DNA fragment containing tyrR was subcloned into pBR322 and used to transform TK453. In the same manner as above, those showing red color in a MacConkey-Lactose medium (Difco) containing 5 mM L-tyrosine were selected. As a result, 3.5-kb fragments could be obtained after digestion with SalI or SphI as DNA fragments carried by the selected strains. Among these, the 3.5 kb SalI fragment was transferred to pUC18 and the nucleotide sequence of the fragment was determined by using a nucleoride sequencer (Shimadzu DSQ-1000L) (SEQ ID NO: 1). An open reading frame was present in this DNA fragment (nucleotide numbers 442–2004) and the amino acid sequence deduced from the sequence (SEQ ID NO: 2) had homology of about 72% with TyrR of *E. coli*.

EXAMPLE 2

Acquisition of Mutant Tyrosine Repressor Gene

<1> Preparation of Host for Measuring Tyrosine Repressor Activity (*E. coli* TK747)

As a host for examining activity of a tyrosine repressor, an *E. coli* strain that lacked the tyrR gene and carried the tpl'-'lac fusion gene on the chromosome was constructed.

(1) Preparation of Strain Lacking tyrR

A 3.9-kb fragment obtained by digesting a plasmid pMU400 containing tyrR derived from *E. coli* (C. Edwina et al., *J. Bacteriol.*, 152, 1276–1279 (1982)) with MluI and MfeI was blunt-ended by using a Takara blunting kit (Takara Shuzo) and the internal region of tyrR was deleted. Separately, pACYC184 (*J. Bacteriol.*, 134, 1141 (1978)) was digested with AccI and HincII and the AccI end was blunt-ended to obtain a fragment containing a chloramphenicol resistant gene (cat). These fragments were ligated to obtain pTK689. The plasmid pTK689 carried a replication regulatory region derived from ColE1, an ampicillin resistant gene (bla) and the tyrR gene of which internal region was replaced with cat (ΔtyrR::cat).

The plasmid pTK689 was digested with HindIII and NdeI and a 3.5-kb fragment containing ΔtyrR::cat was recovered. *E. coli* FS1576 (obtained from National Institute of Genetics (ME9019)) was transformed by using the fragment. Since the FS1576 strain was introduced with recD, the strain was likely to undergo homologous recombination.

A transformed strain showing phenotypes of resistance to 0.2 mM fluorotyrosine and chloramphenicol resistance was selected, and destruction of the tyrR gene was confirmed by PCR using the chromosomal DNA of the obtained transformed strain as a template. Thus, the TK699 strain (recD1009, thi-1, thr-1, leuB6, lacY1, tonA21, supE44, ΔtyrR::cat) was obtained.

(2) Introduction of ΔtyrR::cat and tpl'-'lac Fusion Gene into Host Strain trpDC700::putPA1303::[kan, tpl'-'lac] carried by the TK314 strain incorporated with the tpl'-'lac fusion gene to the chromosome was introduced into *E. coli* CSH26 (ME 8116; obtained from National Institute of Genetics) [F-, ara, Δ(lac-pro), thi] by P1 transduction. Then, ΔtyrR::cat was introduced from the TK699 strain by P1 transduction.

Subsequently, Δ(srl-recA)306::Tn10 was introduced from *E. coli* MV1184 (*Methods in Enzymology*, 153, 3–11 (1987)) to obtain TK747 [F−, ara, Δ(lac-pro), thi, ΔtyrR::cat, trpDC700::putPA1303::[kan, tpl'-'lac], Δ(srl-recA) 306::Tn10].

The TK747 strain obtained as above lacks the tyrR gene and lac operon on the chromosome and carrys the tpl'-'lac fusion gene.

<2> Preparation of Mutant tyrR Gene

A mutation was introduced into a coding region of the tyrR gene of *Erwinia herbicola* by error-prone PCR. An NdeI site was introduced into the translation initiation point of tyrR and a structural gene amplified by PCR was ligated to a region downstream from that site so that the mutation should not be introduced into the promoter region. This procedure was considered to enable expression of a mutant tyrR at the same level as a wild-type tyrR.

Figure 5:
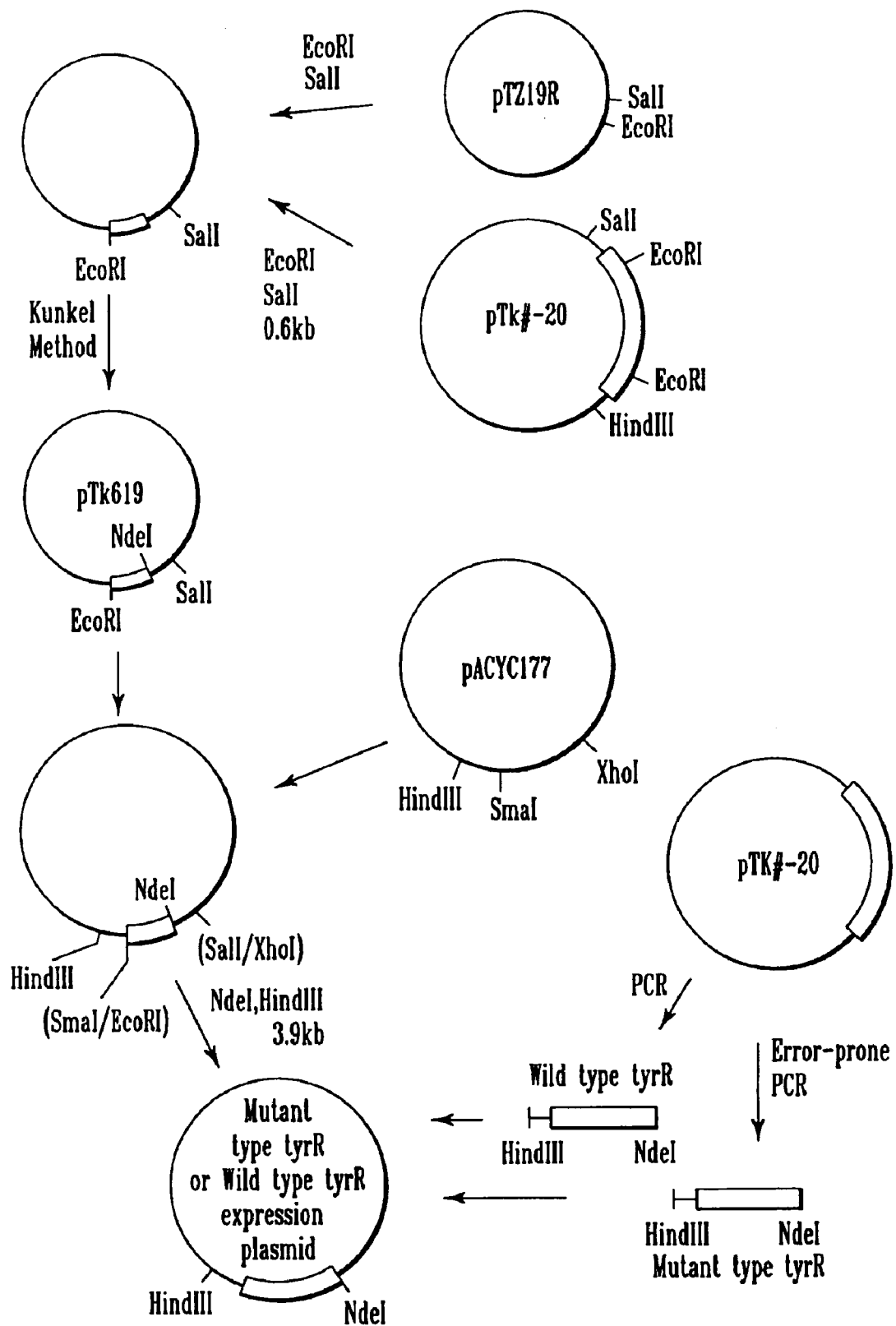
FIG. 5 shows construction of a plasmid expressing a mutant tyrR.

A 0.6-kb SalI-EcoRI fragment containing the promoter region and translation initiation point of tyrR was excised from pTK#-20 and ligated with pTZ19R (Pharmacia) digested with SalI and EcoRI. Then, an NdeI site was introduced into the translation initiation site of tyrR by site-directed mutagenesis using a site-directed mutagenesis kit (Muta-gene phagemid in vitro mutagenesis kit instruction manual (Bio-Rad)) according to the method of Kunkel to obtain pTK619 (FIG. 5). As a primer for introducing the mutation, 5'-gattaaggcccaccatatgcgtttagaag-3' (SEQ ID NO: 9) was used.

The error-prone PCR was performed as follows. A reaction under the conditions of 95° C. for 30 seconds, 55° C. for 30 seconds and 72° C. for 120 seconds were repeated for 25 or 30 cycles by using a reaction solution containing 10 mM Tris-HCl (pH 8.3 at 25° C.), 50 mM KCl, 0.1% Triton X-100, 1.5 mM MgCl$_2$, 0.2 mM dNTPs (mixture containing 0.2 mM each of dATP, dGTP, dCTP and dTTP), 0.1 mM dITP, 100 ng of pTK#-20, 20 pmole each of primers and 2.5 U of rTaq polymerase. As the primers, 5'-gattaaggcccaccatatgcgtttagaag-3' (SEQ ID NO: 10) and 5'-tgagcatgacaaaaagctttacagccag-3' (SEQ ID NO: 11) were used.

The plasmid pTK619 was digested with EcoRI, blunt-ended and then digested with SalI to excise a SalI-EcoRI fragment (0.6 kb). The fragment was inserted between the XhoI and SmaI sites of a single-copy plasmid pACYC177. A 3.9-kb fragment obtained by digesting the obtained plasmid with NdeI and HindIII and a fragment obtained by digesting the mutant tyrR gene amplified by PCR with NdeI and HindIII were ligated to construct a mutant plasmid expressing tyrR (FIG. 5).

Separately, a wild-type plasmid expressing tyrR was constructed as a control. An about 2.4-kb fragment obtained by treating pTK-#20 with SspI and SalI was blunt-ended and inserted into the EcoRV site of pBR322 to prepare pTK561.

<3> Screening of Strains having Increased tpl Transcription Activity

The TK747 strain was transformed by using the plasmid expressing mutant tyrR gene obtained as described above and then inoculated on a basal medium plate (0.5% peptone, 0.5% yeast extract, 0.5% meat extract, 0.2% KH$_2$PO$_4$, pH 8.0) which contained X-gal (5-bromo-4-chloro-3-indolyl-β-D-galactoside) and did not contain tyrosine and cultured at 37° C.

Out of about 90,000 appeared colonies, 100 colonies exhibiting a darker blue color compared with other colonies were selected. Further, these colonies were cultured on the same plate as described above and 5 colonies exhibiting the darkest blue color were selected. The β-galactosidase specific activity in these strains was determined by a known method (Miller, J. H., A short course in bacterial genetics, A laboratory manual and handbook for *Escherichia coli* and related bacteria, Cold Spring Harbor Laboratory Press, Cold Spring Harbor, N.Y. (1992)). Protein was mesured by the method of Lowry (Lowry, O. H. et al., *J. Biol. Chem.* 193, 265 (1951)) by using bovine serum albumin as a reference. Each strain was cultured in a basal medium.

The results are shown in Table 1. In the table, tyrR2, tyrR3 and tyrR4 are the mutant tyrR genes obtained by 25 cycles of PCR and others are those obtained by 30 cycles of PCR.

As a result, the mutant tyrR gene introduced strains showed higher β-galactosidase activity compared with the wild-type tyrR gene introduced strain. Further, all of the tyrR introduced strains including the wild-type introduced strain showed higher β-galactosidase activity than the strains into which no plasmid was introduced.

Amino acid substitutions deduced from each mutation point of the mutant tyrR genes and each mutation are shown in Table 1. In Table 1, numbers in brackets represent the amino acid numbers in SEQ ID NO: 2. Amino acid residues before the mutagenesis are shown on the left of the numbers and amino acid residues after the mutagenesis are shown on the right. It is noted that tyrR5 and tyrR6 had the same mutation.

TABLE 1

| tyrR allele | β-Galactosidase specific activity (Miller U) | Nucleotide mutation and deduced amino acid substitution |
| --- | --- | --- |
| None | 27.4 | |
| Wild-type tyrR | 100 | |
| tyrR2 | 389 | GTC $^{67}$Val → GCC Ala (V67A) |
| | | GTT $^{499}$Val → ATT Ile (V499I) |
| tyrR3 | 393 | GTC $^{67}$Val → GCC Ala (V67A) |
| tyrR4 | 231 | GAT $^{97}$Asp → GGT Gly (D97G) |
| | | ATT $^{402}$Ile → GTT Val (I402V) |
| tyrR5 | 863 | GTC $^{67}$Val → GCC Ala (V67A) |
| | | TAT $^{72}$Tyr → TGT Cys (Y72C) |
| tyrR6 | 850 | GAA $^{201}$Glu → GGA Gly (E201G) |

<4> Separation of Mutation of tyrR Gene having Multiple Mutations and Evaluation of Regulatory Activity for Expression of tpl Promoter While tyrR5 showed the highest tpl promoter inducing activity, since three mutations (V67A, Y72C and E201G) were introduced into tyrR5, mutant tyR5 genes containing each mutation solely or two of them in combination were prepared and activity of each gene was evaluated. Mutations were introduced into tyrR by site-directed mutagenesis. Each obtained mutant tyrR was introduced into the TK747 strain. The transformed strains were cultured in a minimal medium (MM) or a minimal medium containing L-phenylalanine (Phe), L-tryptophan (Trp) or L-tyrosine (Tyr) at 1 mM as a final concentration, and the β-galactosidase specific activity was determined by the aforementioned method of Miller. The results are shown in Table 2. In the table, numbers in brackets represent the activation rates of the β-galactosidase specific activity obtained by Phe, Trp or Tyr added to the medium.

From the results, it can be seen that the V67A mutation, Y72C mutation, V67A and Y72C mutations and V67A, Y72C and E201G mutations, in particlular, increase the tpl promoter inducing activity. Further, the ratio of the β-galactosidase activity in the presence of tyr to the activity in the absence of tyr was the highest in the V67A mutation and the Y72C mutation. In particular, the ratio in the V67A mutation was two fold higher than that in the wild-type tyrR.

TABLE 2

| tyrR allele | β-Galactosidase specific activity (Miller U) | | | |
|---|---|---|---|---|
| | MM | MM + Phe | MM + Trp | MM + Tyr |
| None | 85.3 | 84.6 (1) | 85.6 (1) | 83.8 (1) |
| Wild-type tyrR | 98.0 | 259 (2.6) | 113 (1.2) | 2930 (30) |
| tyrR V67A | 160 | 1030 (6.4) | 208 (1.3) | 9330 (58) |
| tyrR Y72C | 139 | 344 (2.5) | 188 (1.4) | 5060 (36) |
| tyrR E201G | 100 | 259 (2.6) | 112 (1.1) | 3210 (32) |
| tyrR V67A, Y72C | 381 | 1160 (3.0) | 607 (1.6) | 12000 (31) |
| tyrR V67A, Y72C, E201G | 395 | 1210 (3.1) | 647 (1.6) | 12500 (32) |

EXAMPLE 3

Evaluation of Repressor Activity of Mutant TyrR

TyrR is known to negatively regulate expression of genes such as aroF (DAHP synthase gene) and tyrP (tyrosine specific transporter gene) involved in biosynthesis of aromatic amino acids such as tyrosine. Therefore, repressor activity for aroF and tyrP of the mutant Tyr obtained in Example 2 was examined.

The genes aroF and tyrP were amplified by PCR using chromosomal DNA of *E. coli* MG1655 strain (obtained from *E. coli* Genetic Stock Center, Yale University, Dept. Biology, Osborn Memorial Labs., 06511-7444 New Haven, Conn., U.S.A., P.O. Box 6666) as a template and KOD polymerase (Toyobo). As primers, 5'-ccgaattcgctaaatgcatcgtcatctttttatg-3' (SEQ ID NO: 12) and 5'-ccggatcctttgcatgatggcgatcctgttta (SEQ ID NO: 13) were used for aroF, and 5'-ccgaattccagactggcatgcgtatattgc-3' (SEQ ID NO: 14) and 5'-ccggatccttcacgctttcttctgtcctgacga-3' (SEQ ID NO: 15) were used for tyrP. Each amplified fragment included a portion from a region regulated by TyrR to a point slightly downstream from the initiation codon in each gene.

Each amplified fragment was digested with EcoRI and BamHI and cloned between the EcoRI and BamHI sites of pUC19. After the nucleotide sequence was confirmed, the cloned fragment was inserted into pRS552. A fragment containing aroF'-'lac or tyrP'-'lac was excised from the obtained plasmid with HindIII and SalI and inserted between the HindIII and SalI sites of a low copy vector pMW219 (Nippon Gene) to construct pTK588 [pSC101 or, kan, aroF'-'lac] and pTK589 [pSC101 ori, kan, tyrP'-'lac].

Meanwhile, a plasmid expressing tyrR derived from *E. coli* was constructed as follows. An about 2.6-kb fragment was obtained from a plasmid pMU400 (C. Edwina et al., *J. Bacteriol.*, 152, 1276–1279 (1982)) containing tyrR derived from *E. coli* by treatment with NdeI and HindIII. After blunt-ended with T4 DNA polymerase, the fragment was inserted into the EcoRV site of pBR322 (Toyobo) to prepare pTK559.

pTK588 or pTK589 was cotransformed to *E. coli* TK809 [F-, ara, Δ(lac-pro), thi, ΔtyrR::cat, Δ(srl-recA)306::Tn10] (prepared by introducing ΔtyrR::cat from the TK699 strain into the *E. coli* CSH26 strain by P1 transduction and then introducing Δ(srl-recA) 306::Tn10 from the MV1184 strain) together with a mutant tyrR expressing prasmid or pTK559 (*E. coli* tyrR) or pTK561 (wild-type tyrR of *E. herbicola*). The β-galactosidase specific activity of the obtained transformed strains was examined in the same manner as in Example 2 <4>. The results are shown in Table 3 (aroF) and Table 4 (tyrP).

It was found from these results that each mutant TyrR had lower inhibitory activity for expression of the aroF gene and tyrP gene and reduced repressor activity compared with those of the wild-type TyrR.

TABLE 3

Expression of aroF'—'lac

| tyrR allele | β-Galactosidase specific activity (Miller U) | | | |
|---|---|---|---|---|
| | MM | MM + Phe | MM + Trp | MM + Tyr |
| None | 900 | 910 | 909 | 908 |
| Wild-type tyrR (*E. coli*) | 546 | 230 | 540 | 28.6 |
| Wild-type tyrR (*E. herbicola*) | 534 | 279 | 486 | 31.4 |
| TyrR V67A | 651 | 281 | 726 | 42.9 |
| TyrR Y72C | 842 | 332 | 898 | 42.3 |
| TyrR E201G | 558 | 363 | 529 | 32.7 |
| TyrR V67A, Y72C, E201G | 903 | 388 | 982 | 61.9 |

TABLE 4

Expression of tyrP'—'lac

| tyrR allele | β-Galactosidase specific activity (Miller U) | | | |
|---|---|---|---|---|
| | MM | MM + Phe | MM + Trp | MM + Tyr |
| None | 44.0 | 43.9 | 44.0 | 43.6 |
| Wild-type tyrR (*E. coli*) | — | — | — | — |
| Wild-type tyrR (*E. herbicola*) | 19.0 | 22.6 | 21.2 | <1 |
| TyrR V67A | 46.9 | 31.0 | 55.2 | <2 |
| TyrR Y72C | 28.0 | 30.9 | 41.4 | <1 |
| TyrR E201G | 19.1 | 31.3 | 23.4 | <1 |
| TyrR V67A, Y72C, E201G | 69.1 | 51.2 | 78.6 | <3 |

EXAMPLE 4

Introduction of Mutant tyrR into *Erwinia herbicola*

<1> Preparation of *Erwinia herbicola* tyrR Deleted Strain

A plasmid having the longest inserted fragment among the plasmids of the candidate strains harboring the tyrR gene obtained in Example 1 <3> was designated as pTK#-13. pTK#-13 was digested with EcoRI to recover 5.5-kb and 6.5-kb fragments, which were ligated with a 1.3-kb fragment containing the kanamycin resistant gene (kan) produced by digesting pUC4K (Pharmacia Biotech) with EcoRI to obtain pTK766 [ColEIori, bla, ΔtyrR::kan]. In this plasmid, almost the whole region of the tyrR gene was replaced with the kanamycin resistant gene.

When this plasmid was digested with FspI, four sites on the vector side and one site in the inserted fragment were digested, and a fragment having 4-kb and 2.2-kb homologous regions on both sides of the kan gene was produced. This fragment was recovered and introduced into the AJ2985 strain of *Erwinia herbicola* (ATCC21434) by electroporation (Methods for general and molecular bacteriology, 1994, Philipp Gerhardt ed., ASM Press, 14.1.3.3 Electroporation procedure). The electroporation was carried out by adding 0.25 μl of cells into a 0.2-cm cuvette and applying pulses of 25 μF, 2.5 kV and 200 Ω.

The transformed cells were cultured for one hour, and inoculated on an LB plate containing 30 μg/ml of kanamycin. The grown strains were examined for the presence of the plasmid, and three strains having no plasmid were obtained.

When the obtained three strains were subjected to Western blotting using anti-tyrosine phenol lyase antibodies, no strain expressed tyrosine phenol lyase. One strain among those strains was subjected to genomic Southern blotting to confirm that tyrR was replaced with ΔtyrR::kan. This strain was designated as YG17.

The anti-tyrosine phenol lyase antibodies were prepared as follows. Tyrosine phenol lyase (TPL) was purified from a cell-free extract of *Erwinia herbicola*. A female New Zealand white rabbit was immunized by using 1 mg TPL emulsified in Freund's complete adjuvant. Booster immunization was performed twice at two-week intervals by using 1 mg TPL emulsified in Freund's complete adjuvant. A small amount of blood was collected after each booster immunization to examine anti-TPL activity. The whole blood was collected and allowed to stand at 37° C. for 1 hour. Then, the blood was centrifuged to remove blood clot to obtain crude antiserum. An immunoglobulin G fraction was purified from the crude antiserum by protein-A Sepharose CL-6B (Pharmacia) column chromatography according to the method described in the manufacturer's instruction.

Figure 6:
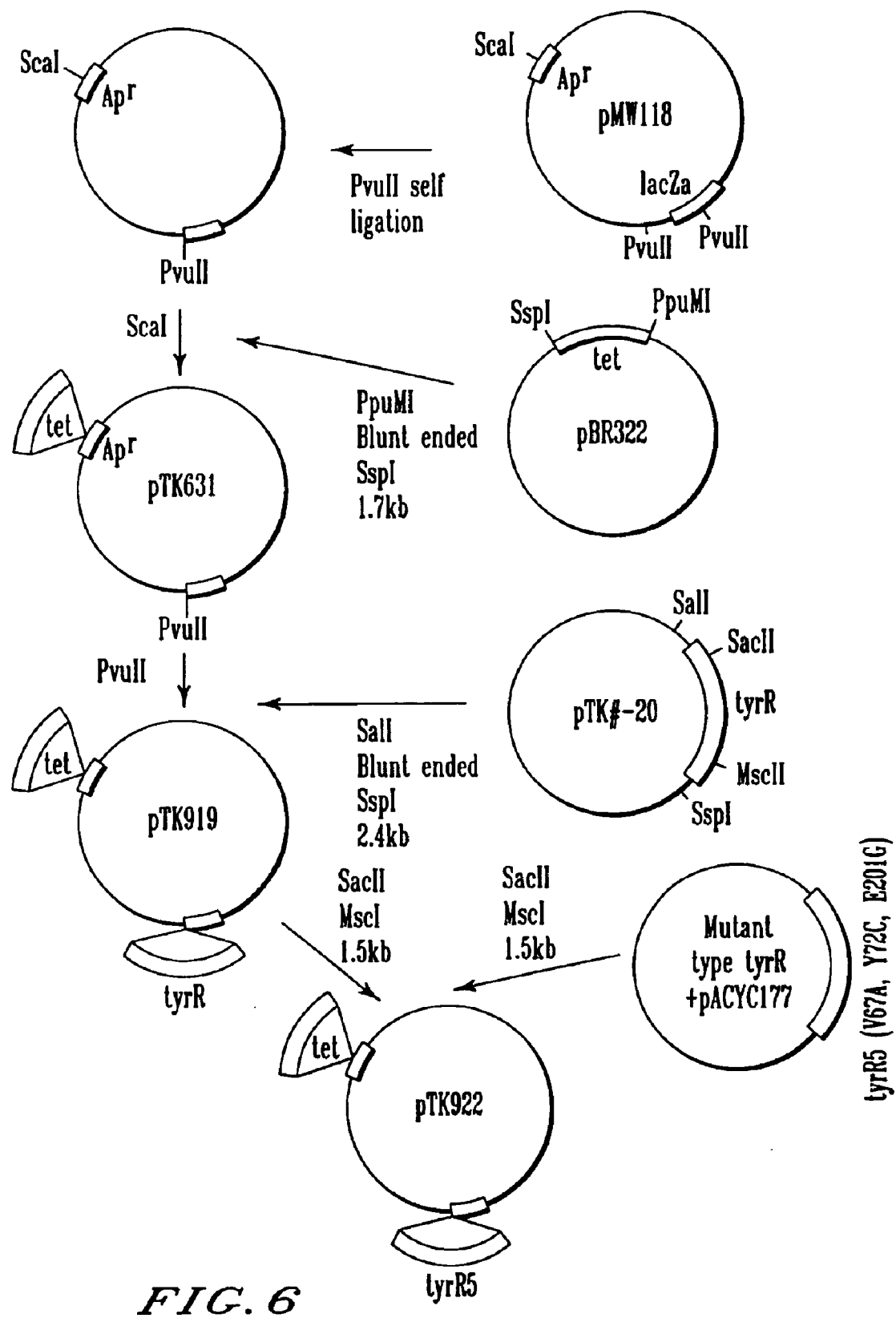
FIG. 6 shows construction of a plasmid pTK922 for introducing the mutant tyrR into *Erwinia herbicola*.

<2> Construction of Plasmid for Introducing Mutant tyrR pMW118 (Nippon Gene) was digested with PvuII and self-ligated to remove the lacZ gene. The obtained plasmid was digested with ScaI. The tetracycline resistant gene (tet) excised from pBR322 by digestion with SspI and PpuMI was blunt-ended and then inserted into the above plasmid to obtain pTK631. Subsequently, pTK631 and pTK#-20 were digested with PvuII and SalI, respectively, blunt-ended, and inserted with a tyrR gene fragment excised by digesting with SspI to obtain pTK919. Further, pTK919 was digested with SacII and MscI to recover a 6.3-kb fragment and inserted with a fragment obtained by digesting pACYC177 inserted with a mutant tyrR (tyrR5) fragment having V67A, Y72C and E201G mutations with SacII and MscI to obtain pTK922 (FIG. 6).

<3> Evaluation of Tyrosine Phenol Lyase Activity of Mutant tyrR Introduced Strain The plasmids pTK919 [pSC101 ori, bla::tet, tyrR] and pTK922 [pSC101 ori, bla::tet, tyrR V67A, Y72C, E201G] obtained as described above were introduced into the YG17 strain to obtain the YG38 strain and the YG40 strain, respectively. These strains were cultured overnight at 30° C. in 100 ml of the basal medium containing 0.1% tyrosine. The microbial cells were suspended in 10 mM potassium phosphate buffer (pH 7.0), 0.2 mM PLP (pyridoxal 5'-phosphate), 5 mM 2-mercaptoethnol and 4 mM EDTA (pH 7.0) and disrupted by sonication. The suspension containing the disrupted microbial cells was dialyzed against the buffer overnight. The amount of protein and tyrosine phenol lyase activity in the crude enzyme solution obtained as described above were determined.

The mesurement of protein was performed by using bovine serum albumin as a reference according to the method of Lowry (Lowry, O. H. et al., *J. Biol. Chem.*, 193, 265 (1951)). The tyrosine phenol lyase activity was determined as follows. A reaction solution containing 1 mM tyrosine , 0.1 mM PLP, 0.078 mM NADH, 0.1 mM 2-mercaptoethanol, lactate dehydrogenase (derived from rabbit muscle, 1.3 I.U./ml) in 100 mM potassium phosphate buffer (pH 8.0) was preincubated at 30° C., and added with 10–100 μl of a sample, and oxidation of NADH was traced by monitoring absorption at 340 nm. consumption of NADH corresponded to consumption of tyrosine by 1:1. The amount of enzyme consuming 1 μM of tyrosine for 1 minute was defined as 1 unit. The results are shown in Table 5.

From the results, the strain of *Erwinia herbicola* into which a mutant tyrR was introduced exhibited a higher tyrosine phenol lyase activity than the strain into which a wild-type tyrR was introduced. The *Erwinia herbicola* strains into which a mutant tyrR was introduced exhibited a high tyrosine phenol lyase activity even when tyrosine was not added to medium.

TABLE 5

| tyrR allele | Tyrosine phenol lyase specific activity (U) | |
| --- | --- | --- |
| | MM | MM + Tyr |
| YG38 | 5.73 | 22.5 |
| YG40 | 22.8 | 44.3 |

What is claimed is:

1. An isolated mutant tyrosine repressor, wherein the unmutated tyrosine repressor has an amino acid sequence that is at least 80% identical to SEQ ID NO: 2, said repressor having one or more mutations selected from the group consisting of:
   a) a replacement of the valine residue at position 67 corresponding to SEQ ID NO: 2 with an amino acid other than valine;
   b) a replacement of the tyrosine residue at position 72 corresponding to SEQ ID NO: 2 with an amino acid other than tyrosine; and
   c) a replacement of the aspartic acid residue at position 97 corresponding to SEQ ID NO: 2 with an amino acid other than aspartic acid;
   wherein the mutant tyrosine repressor has an increased positive regulatory activity for expression of tyrosine phenol lyase gene compared with the tyrosine repressor not having the one or more mutations,
   wherein the mutant tyrosine repressor is encoded by a DNA which hybridizes to SEQ ID NO: 1 under stringent conditions, and wherein said stringent conditions comprise 1×SSC, 01% SDS at 65° C.

2. The isolated mutant tyrosine repressor according to claim 1, wherein the mutation is the replacement of the valine residue at position 67 corresponding to SEQ ID NO: 2 with an amino acid other than valine.

3. The isolated mutant tyrosine repressor according to claim 1, wherein the valine residue at position 67 is replaced with alanine.

4. The isolated mutant tyrosine repressor according to claim 3, which further comprises a replacement of the tyrosine residue at position 72 corresponding to SEQ ID NO: 2 with a cysteine.

5. The isolated mutant tyrosine repressor according to claim 4, which further comprises a replacement of the glutamic acid residue at position 201 with a glycine.

6. The isolated mutant tyrosine repressor according to claim 1, wherein the mutation is the replacement of the tyrosine residue at position 72 corresponding to SEQ ID NO: 2 with an amino acid other than tyrosine.

7. The isolated mutant tyrosine repressor according to claim 6, wherein the tyrosine is replaced with a cysteine.

8. The isolated mutant tyrosine repressor according to claim 1, wherein the mutation is the replacement of the aspartic acid residue at position 97 corresponding to SEQ ID NO: 2 with an amino acid other than aspartic acid.

9. The isolated mutant tyrosine repressor according to claim 8, wherein the aspartic acid is replaced with a glycine.

10. The isolated mutant tyrosine repressor according to claim 1, wherein the unmutated tyrosine repressor has an amino acid sequence of SEQ ID NO: 2.

11. The isolated mutant tyrosine repressor according to claim 2, wherein the unmutated repressor has an amino acid sequence of SEQ ID NO: 2.

12. The isolated mutant tyrosine repressor according to claim 3, wherein the unmutated repressor has an amino acid sequence of SEQ ID NO: 2.

13. The isolated mutant tyrosine repressor according to claim 4, wherein the unmutated repressor has an amino acid sequence of SEQ ID NO: 2.

14. The isolated mutant tyrosine repressor according to claim 5, wherein the unmutated repressor has an amino acid sequence of SEQ ID NO: 2.

15. The isolated mutant tyrosine repressor according to claim 6, wherein the unmutated repressor has an amino acid sequence of SEQ ID NO: 2.

16. The isolated mutant tyrosine repressor according to claim 7, wherein the unmutated repressor has an amino acid sequence of SEQ ID NO: 2.

17. The isolated mutant tyrosine repressor according to claim 8, wherein the unmutated repressor has an amino acid sequence of SEQ ID NO: 2.

18. The isolated mutant tyrosine repressor according to claim 9, wherein the unmutated repressor has an amino acid sequence of SEQ ID NO: 2.

* * * * *

SEQUENCE LISTING

<160> NUMBER OF SEQ ID NOS: 15

<210> SEQ ID NO 1
<211> LENGTH: 3363
<212> TYPE: DNA
<213> ORGANISM: Erwinia herbicola
<220> FEATURE:
<221> NAME/KEY: CDS
<222> LOCATION: (442)..(2004)

<400> SEQUENCE: 1

```
gtcgacgcgt gccgcagggc attggtgcgg ggctgctcac cgcccggctg ggtatcaaag      60
cgatggagct gtgtcggcct ttaccctggc tggaaaatga taaacctcgt ctcggcgatt     120
accgcgggag ctgttagggc agttgaaaga cgcgctacaa aagggcggga ataaacatcc     180
acaaaactga ctttagatgg ggccgttatt taacgtcccc tgtttagcgc gccaaatctg     240
cgggggaccg ttccgggata ctgggaagat taactgcgaa agacgtcgaa aactcaaggt     300
```

-continued

```
gttatggcgc gctgcgcgcg acggacgttt aaaaaaaacg cgcttgcgtt aacgctgtca        360
acttttcctg acagcccct ttctgcggac gggctgttta gcgtattatc gcgacatatc         420
aaacggatta aggcccacgc a atg cgt tta gaa gtg ttt tgt cag gac cgt          471
                        Met Arg Leu Glu Val Phe Cys Gln Asp Arg
                         1               5                  10 atc gga ctg gcg cgt gaa ttg ctc gac ctg ttg gtg gcg cgc agt atc          519
Ile Gly Leu Ala Arg Glu Leu Leu Asp Leu Leu Val Ala Arg Ser Ile
             15                  20                  25 gat ctc cgc ggc att gaa gtc gcc gcc tca ggc cgt atc tat ctt aat          567
Asp Leu Arg Gly Ile Glu Val Ala Ala Ser Gly Arg Ile Tyr Leu Asn
         30                  35                  40 ttc tcc acg ctt gaa ttc gaa cag ttc agt aat ctg atg gcg gaa atc          615
Phe Ser Thr Leu Glu Phe Glu Gln Phe Ser Asn Leu Met Ala Glu Ile
             45                  50                  55 cgt cgt aca ccc ggc gtc acc gat gtc cgc acg gtc ccc tat atg ccg          663
Arg Arg Thr Pro Gly Val Thr Asp Val Arg Thr Val Pro Tyr Met Pro
         60                  65                  70 tct gaa cgt gaa cat cgg gta ctc agc gcc ttg ctg gtt gcc atg cca          711
Ser Glu Arg Glu His Arg Val Leu Ser Ala Leu Leu Val Ala Met Pro
 75              80                  85                  90 gag ccg gta ttt tcg gtt gat ttg aga acg aag gtt gag ctg gcg aac          759
Glu Pro Val Phe Ser Val Asp Leu Arg Thr Lys Val Glu Leu Ala Asn
                 95                 100                 105 ccg gcg gcg caa aac ctg ttt aat ctt gat gaa aac aag atc cgc aat          807
Pro Ala Ala Gln Asn Leu Phe Asn Leu Asp Glu Asn Lys Ile Arg Asn
             110                 115                 120 ttt acc gcc gac cac ctg att aac ggt ttt aat ttt gcg cgc tgg ctg          855
Phe Thr Ala Asp His Leu Ile Asn Gly Phe Asn Phe Ala Arg Trp Leu
         125                 130                 135 gag agc gaa cgc gtt cag gcg cag gcg caa cat gtg gtg ata gaa ggg          903
Glu Ser Glu Arg Val Gln Ala Gln Ala Gln His Val Val Ile Glu Gly
     140                 145                 150 cgc gac ttc ctg atg gaa gca cac ccg att tac ctg tca gag gac aac          951
Arg Asp Phe Leu Met Glu Ala His Pro Ile Tyr Leu Ser Glu Asp Asn
155                 160                 165                 170 gac cag gcc gac cag ctc gtc ggc gca atg gtg atg ctg aag tct act          999
Asp Gln Ala Asp Gln Leu Val Gly Ala Met Val Met Leu Lys Ser Thr
                 175                 180                 185 gcc cgt atg ggg cga caa ctg cag aac ctg gtg gtg acc gat gaa acc         1047
Ala Arg Met Gly Arg Gln Leu Gln Asn Leu Val Val Thr Asp Glu Thr
             190                 195                 200 gag ttc gat cat att gtc gcc gtt acg ccc agg atg cgg cag gtc gtg         1095
Glu Phe Asp His Ile Val Ala Val Thr Pro Arg Met Arg Gln Val Val
         205                 210                 215 gaa cag gcg cgc aag ctc gcg atg cac gat gca ccg ctg ctg att atc         1143
Glu Gln Ala Arg Lys Leu Ala Met His Asp Ala Pro Leu Leu Ile Ile
     220                 225                 230 ggc gac acc ggc acg ggc aaa gac atg ctg gcg cgg gcc tgt cat tta         1191
Gly Asp Thr Gly Thr Gly Lys Asp Met Leu Ala Arg Ala Cys His Leu
235                 240                 245                 250 cgc agc gca cgc gga aag atg cct ttt ctg gcg ctt aac tgt gca tcg         1239
Arg Ser Ala Arg Gly Lys Met Pro Phe Leu Ala Leu Asn Cys Ala Ser
                 255                 260                 265 ctg ccg gat gac gta gcg gaa agt gag ctt ttt ggt cac gca gcc ggg         1287
Leu Pro Asp Asp Val Ala Glu Ser Glu Leu Phe Gly His Ala Ala Gly
             270                 275                 280 gcc tat ccc aat gcg ctg gag ggc aaa aaa ggc ttt ttc gaa cag gca         1335
Ala Tyr Pro Asn Ala Leu Glu Gly Lys Lys Gly Phe Phe Glu Gln Ala
```

-continued

```
              285                 290                 295
aac ggt ggc tcg gtg ctg ctg gat gaa att ggc gag atg tca ccc act    1383
Asn Gly Gly Ser Val Leu Leu Asp Glu Ile Gly Glu Met Ser Pro Thr
            300                 305                 310 atg cag acg aag ctg ctg cgt ttt ctg aac gat ggc act ttc cgc cgc    1431
Met Gln Thr Lys Leu Leu Arg Phe Leu Asn Asp Gly Thr Phe Arg Arg
315                 320                 325                 330 gtc ggt gag gag cat gag gta cac gtg aat gtc cgc gtg atc tgc gcc    1479
Val Gly Glu Glu His Glu Val His Val Asn Val Arg Val Ile Cys Ala
                335                 340                 345 acc cag aag aac ctg ttt gag ctg gtt cag cgc ggc gag ttc agg gaa    1527
Thr Gln Lys Asn Leu Phe Glu Leu Val Gln Arg Gly Glu Phe Arg Glu
            350                 355                 360 gac ctt ttc tat cgc ctg aat gtg ctt acg ctg aat ctg ccg ccg ctg    1575
Asp Leu Phe Tyr Arg Leu Asn Val Leu Thr Leu Asn Leu Pro Pro Leu
            365                 370                 375 cgc gag cgc gtt cag gac att atg ccg ctg acg gaa att ttc gtg gcg    1623
Arg Glu Arg Val Gln Asp Ile Met Pro Leu Thr Glu Ile Phe Val Ala
            380                 385                 390 cgt ttc gcc gat gaa cag ggc att cct cgg ccg cgt ctt tcc tca cag    1671
Arg Phe Ala Asp Glu Gln Gly Ile Pro Arg Pro Arg Leu Ser Ser Gln
395                 400                 405                 410 ctg aat gct ttt ctg atg cgc tat aac tgg ccc gga aac gtg cgg cag    1719
Leu Asn Ala Phe Leu Met Arg Tyr Asn Trp Pro Gly Asn Val Arg Gln
                415                 420                 425 ctt aaa aat gcc ttg tat cgt gca tta acc cag ttg gaa ggc cat gag    1767
Leu Lys Asn Ala Leu Tyr Arg Ala Leu Thr Gln Leu Glu Gly His Glu
            430                 435                 440 tta cgg ccg cag gat atc gtc ttg ccg gaa cag gcg ctg gat gtg tca    1815
Leu Arg Pro Gln Asp Ile Val Leu Pro Glu Gln Ala Leu Asp Val Ser
            445                 450                 455 ctg ggg gaa gaa gcg atg gaa ggc acg ctg gat cag atc acc agc cgc    1863
Leu Gly Glu Glu Ala Met Glu Gly Thr Leu Asp Gln Ile Thr Ser Arg
            460                 465                 470 ttt gaa cga tct att ttg acg cgg tta tat ttg tct tat ccg agc acg    1911
Phe Glu Arg Ser Ile Leu Thr Arg Leu Tyr Leu Ser Tyr Pro Ser Thr
475                 480                 485                 490 cgc aaa ctg gca aaa cga ctg ggg gtt tcc cat acc gcc att gcc aat    1959
Arg Lys Leu Ala Lys Arg Leu Gly Val Ser His Thr Ala Ile Ala Asn
                495                 500                 505 aaa ctg cgt gag tac ggt ctg ggg cag aag cgc ggc gac aac gaa        2004
Lys Leu Arg Glu Tyr Gly Leu Gly Gln Lys Arg Gly Asp Asn Glu
            510                 515                 520 taaaacgcag cggataagtc tggcttatcc gctgtggcca ttatttcagc gcagcgagtg    2064
cggcatcata atcgggttca gtggtgatct cattcaccag ctggctgtaa agcactttgt    2124
catgctcatc cagtacgata acggcacggg ccgtcagacc ctgaagggca ccatcagcaa    2184
tttccacgcc aaaatctttt ttgaattccc gccgcgcag cgttgacagc gtaaccacgt     2244
tgttgaggtt gtctgcgcca caaaaacgcg attgagcaaa gggcaggtcg gcggaaatac    2304
ataacaccac cgtgttattc agttcgcccg ctaactggtt aaacttgcgc accgaagagg    2364
cgcacacgcc ggtatcgacg ctgggaaaaa tattcagaat cttgcgtttt cctgcatact    2424
cagagagtga aacgttagac aggttttttcg ccacgagggt aaaagcgtta acgctatcgc    2484
ccggctgcgg gaactgacct gcaaccgcta cagggttgcc ctgaaagtga acagtctgag    2544
acataagaat tccttctaat gatgttatct gacagaaaag aaaagcgtcag tacaggtata    2604 gccattgttt atgacataaa ttttaagggt ttacgagagc atttgttgcc taaagttaaa    2664
```

-continued

```
tggcgatgat gaatcccaga gaaaggaga ggtaatgaga acggtaaaat gttatcccga    2724
agcatggccg ctgcatacgc cgtttgtcat tgctcgtggc agtcgcaccg aagccaaggt    2784
cgttgtcgtc gaaatcgaag aagagggcgt gaaagggatc ggcgaggcca cgccttacac    2844
gcgctacggc gaaagcgaag ccctggtgct ggaacaaatt gcgaccgtta tgcctcaact    2904
gcagcaaggg ctgtcgcgtg aagccttgca gagcctgttg cctgccggtg cggcaagaaa    2964
cgccatcgac agtgctctct ggaccttgc cgctcgccag cagcatgtga cgctggagca    3024
gttagtgggc gcggaaccga cccagtctgt tgtgactgca cacacggtga gcattgatac    3084
gccggaagcg atggccagca gcgcgcaggc gttgtggcaa catggcgcaa cactgctcaa    3144
aatcaaaatg gacaataact ttattaccga gcgcctgatg gcgattcgcg ctgctgttcc    3204
cgacgcgaca ttacttgtgg atgcgaatga atcctggcat gccgaaggct ggcagcccgt    3264
tgccagctgt tagccgatct ggaggtggcc atgctggaac agccgttacc ggcaggtgaa    3324
gacgcggcgc tggcgaactt tatccatcct cttccgatc                           3363
```

<210> SEQ ID NO 2
<211> LENGTH: 521
<212> TYPE: PRT
<213> ORGANISM: Erwinia herbicola

<400> SEQUENCE: 2

```
Met Arg Leu Glu Val Phe Cys Gln Asp Arg Ile Gly Leu Ala Arg Glu
1               5                   10                  15

Leu Leu Asp Leu Leu Val Ala Arg Ser Ile Asp Leu Arg Gly Ile Glu
                20                  25                  30

Val Ala Ala Ser Gly Arg Ile Tyr Leu Asn Phe Ser Thr Leu Glu Phe
            35                  40                  45

Glu Gln Phe Ser Asn Leu Met Ala Glu Ile Arg Arg Thr Pro Gly Val
        50                  55                  60

Thr Asp Val Arg Thr Val Pro Tyr Met Pro Ser Glu Arg Glu His Arg
65                  70                  75                  80

Val Leu Ser Ala Leu Leu Val Ala Met Pro Glu Pro Val Phe Ser Val
                85                  90                  95

Asp Leu Arg Thr Lys Val Glu Leu Ala Asn Pro Ala Ala Gln Asn Leu
            100                 105                 110

Phe Asn Leu Asp Glu Asn Lys Ile Arg Asn Phe Thr Ala Asp His Leu
        115                 120                 125

Ile Asn Gly Phe Asn Phe Ala Arg Trp Leu Glu Ser Glu Arg Val Gln
    130                 135                 140

Ala Gln Ala Gln His Val Val Ile Glu Gly Arg Asp Phe Leu Met Glu
145                 150                 155                 160

Ala His Pro Ile Tyr Leu Ser Glu Asp Asn Asp Gln Ala Asp Gln Leu
                165                 170                 175

Val Gly Ala Met Val Met Leu Lys Ser Thr Ala Arg Met Gly Arg Gln
            180                 185                 190

Leu Gln Asn Leu Val Val Thr Asp Glu Thr Glu Phe Asp His Ile Val
        195                 200                 205

Ala Val Thr Pro Arg Met Arg Gln Val Val Glu Gln Ala Arg Lys Leu
    210                 215                 220

Ala Met His Asp Ala Pro Leu Leu Ile Ile Gly Asp Thr Gly Thr Gly
225                 230                 235                 240

Lys Asp Met Leu Ala Arg Ala Cys His Leu Arg Ser Ala Arg Gly Lys
```

-continued

```
                    245                 250                 255
Met Pro Phe Leu Ala Leu Asn Cys Ala Ser Leu Pro Asp Asp Val Ala
            260                 265                 270

Glu Ser Glu Leu Phe Gly His Ala Ala Gly Ala Tyr Pro Asn Ala Leu
        275                 280                 285

Glu Gly Lys Lys Gly Phe Phe Glu Gln Ala Asn Gly Gly Ser Val Leu
    290                 295                 300

Leu Asp Glu Ile Gly Glu Met Ser Pro Thr Met Gln Thr Lys Leu Leu
305                 310                 315                 320

Arg Phe Leu Asn Asp Gly Thr Phe Arg Arg Val Gly Glu Glu His Glu
                325                 330                 335

Val His Val Asn Val Arg Val Ile Cys Ala Thr Gln Lys Asn Leu Phe
            340                 345                 350

Glu Leu Val Gln Arg Gly Glu Phe Arg Glu Asp Leu Phe Tyr Arg Leu
        355                 360                 365

Asn Val Leu Thr Leu Asn Leu Pro Pro Leu Arg Glu Arg Val Gln Asp
    370                 375                 380

Ile Met Pro Leu Thr Glu Ile Phe Val Ala Arg Phe Ala Asp Glu Gln
385                 390                 395                 400

Gly Ile Pro Arg Pro Arg Leu Ser Ser Gln Leu Asn Ala Phe Leu Met
                405                 410                 415

Arg Tyr Asn Trp Pro Gly Asn Val Arg Gln Leu Lys Asn Ala Leu Tyr
            420                 425                 430

Arg Ala Leu Thr Gln Leu Glu Gly His Glu Leu Arg Pro Gln Asp Ile
        435                 440                 445

Val Leu Pro Glu Gln Ala Leu Asp Val Ser Leu Gly Glu Glu Ala Met
    450                 455                 460

Glu Gly Thr Leu Asp Gln Ile Thr Ser Arg Phe Glu Arg Ser Ile Leu
465                 470                 475                 480

Thr Arg Leu Tyr Leu Ser Tyr Pro Ser Thr Arg Lys Leu Ala Lys Arg
                485                 490                 495

Leu Gly Val Ser His Thr Ala Ile Ala Asn Lys Leu Arg Glu Tyr Gly
            500                 505                 510

Leu Gly Gln Lys Arg Gly Asp Asn Glu
        515                 520
```

<210> SEQ ID NO 3
<211> LENGTH: 11
<212> TYPE: DNA
<213> ORGANISM: Erwinia herbicola

<400> SEQUENCE: 3
atgaactatc c                                                          11

<210> SEQ ID NO 4
<211> LENGTH: 11
<212> TYPE: DNA
<213> ORGANISM: Erwinia herbicola

<400> SEQUENCE: 4
atggaggatc c                                                          11

<210> SEQ ID NO 5
<211> LENGTH: 11
<212> TYPE: DNA
<213> ORGANISM: Erwinia herbicola -continued

```
<400> SEQUENCE: 5
ttaacattcg c                                                            11

<210> SEQ ID NO 6
<211> LENGTH: 11
<212> TYPE: DNA
<213> ORGANISM: Erwinia herbicola

<400> SEQUENCE: 6
ttagaattcg c                                                            11

<210> SEQ ID NO 7
<211> LENGTH: 22
<212> TYPE: DNA
<213> ORGANISM: Erwinia herbicola

<400> SEQUENCE: 7
tcggcaggat ccttcatgtt ta                                                22

<210> SEQ ID NO 8
<211> LENGTH: 22
<212> TYPE: DNA
<213> ORGANISM: Erwinia herbicola

<400> SEQUENCE: 8
agcggcgaat tctaatgacg tg                                                22

<210> SEQ ID NO 9
<211> LENGTH: 29
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 9
gattaaggcc caccatatgc gtttagaag                                         29

<210> SEQ ID NO 10
<211> LENGTH: 29
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 10
gattaaggcc caccatatgc gtttagaag                                         29

<210> SEQ ID NO 11
<211> LENGTH: 28
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 11
tgagcatgac aaaaagcttt acagccag                                          28

<210> SEQ ID NO 12
<211> LENGTH: 33
```

```
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 12
ccgaattcgc taaatgcatc gtcatctttt atg                              33

<210> SEQ ID NO 13
<211> LENGTH: 33
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 13
ccggatcctt ttgcatgatg gcgatcctgt tta                              33

<210> SEQ ID NO 14
<211> LENGTH: 30
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 14
ccgaattcca gactggcatg cgtatattgc                                  30

<210> SEQ ID NO 15
<211> LENGTH: 33
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 15
ccggatcctt cacgctttct tctgtcctga cga                              33
```